(12) United States Patent
Chamas et al.

(10) Patent No.: US 12,048,444 B2
(45) Date of Patent: Jul. 30, 2024

(54) INTERVENTIONAL MEDICAL DEVICE HAVING REDUCED FRACTURE RISK

(71) Applicant: C. R. Bard, Inc., Franklin Lakes, NJ (US)

(72) Inventors: Faith C. Chamas, Scottsdale, AZ (US); Hiep Q. Do, Chandler, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 742 days.

(21) Appl. No.: 16/636,807

(22) PCT Filed: Aug. 30, 2017

(86) PCT No.: PCT/US2017/049372
§ 371 (c)(1),
(2) Date: Feb. 5, 2020

(87) PCT Pub. No.: WO2019/045705
PCT Pub. Date: Mar. 7, 2019

(65) Prior Publication Data
US 2020/0367918 A1   Nov. 26, 2020

(51) Int. Cl.
*A61B 17/22* (2006.01)
*A61B 17/00* (2006.01)
*A61F 2/01* (2006.01)

(52) U.S. Cl.
CPC ........ *A61B 17/2202* (2013.01); *A61F 2/0105* (2020.05); *A61B 2017/00853* (2013.01); *A61B 2017/22021* (2013.01)

(58) Field of Classification Search
CPC ...... A61B 17/2202; A61B 2017/00853; A61B 2017/22021; A61F 2/0105
See application file for complete search history.

(56) References Cited

U.S. PATENT DOCUMENTS

| | | | |
|---|---|---|---|
| 4,811,743 A | | 3/1989 | Stevens |
| 5,387,190 A | * | 2/1995 | Gotanda .......... A61B 17/22012 606/1 |
| 5,971,949 A | | 10/1999 | Levin et al. |

(Continued)

FOREIGN PATENT DOCUMENTS

| | | |
|---|---|---|
| EP | 2967606 A2 | 1/2016 |
| JP | 2003521309 A | 7/2003 |

(Continued)

OTHER PUBLICATIONS

Office Action dated Oct. 21, 2022, pertaining to Chinese Application 201780094378.4.

(Continued)

*Primary Examiner* — Sean A Frith
(74) *Attorney, Agent, or Firm* — Dinsmore & Shohl LLP

(57) ABSTRACT

An interventional medical device, and method of manufacturing the same, is provided to reduce risk to the patient of a fracture of the interventional medical device. At least one portion of the interventional medical device that is subject to fracture and migration within a patient is identified. A membrane is applied over each portion of the interventional medical device that is subject to fracture and migration, such that any fractured portion of the interventional medical device is tied together by the membrane.

14 Claims, 3 Drawing Sheets

(56) References Cited

U.S. PATENT DOCUMENTS

| | | | |
|---|---|---|---|
| 6,450,975 | B1 | 9/2002 | Brennan et al. |
| 7,384,407 | B2 | 6/2008 | Rodriguez et al. |
| 8,932,223 | B2 | 1/2015 | Emelianov et al. |
| 2001/0039431 | A1 | 11/2001 | DeVries et al. |
| 2005/0015953 | A1* | 1/2005 | Keidar ............... A61B 17/2202 29/829 |
| 2006/0069405 | A1 | 3/2006 | Schaeffer et al. |
| 2007/0260172 | A1* | 11/2007 | Nita ................... A61B 17/2202 604/22 |
| 2008/0300620 | A1 | 12/2008 | Chanduszko |
| 2013/0023897 | A1* | 1/2013 | Wallace ........... A61B 17/22004 606/128 |
| 2013/0035628 | A1 | 2/2013 | Garrison et al. |
| 2013/0211292 | A1* | 8/2013 | Sverdlik ................ A61B 8/445 601/2 |
| 2013/0296903 | A1* | 11/2013 | Nita ................... A61M 25/0082 606/159 |
| 2014/0107534 | A1* | 4/2014 | Du ................... A61B 17/22012 601/2 |
| 2014/0214064 | A1* | 7/2014 | Nita ................. A61B 17/22012 606/169 |
| 2016/0022306 | A1 | 1/2016 | Du et al. |
| 2016/0220269 | A1 | 8/2016 | Labropoulos et al. |
| 2016/0331645 | A1* | 11/2016 | Bagwell ........... A61B 17/22012 |

FOREIGN PATENT DOCUMENTS

| | | |
|---|---|---|
| JP | 2008513147 A | 5/2008 |
| WO | 9211815 A2 | 7/1992 |
| WO | 2001054617 A1 | 8/2001 |
| WO | 2003034233 A1 | 4/2003 |
| WO | 2006061829 A1 | 6/2006 |
| WO | 2008150863 A1 | 12/2008 |
| WO | 2016081026 A1 | 5/2016 |

OTHER PUBLICATIONS

Office Action dated Mar. 27, 2023 pertaining to Japanese Patent Application No. 2022 080078.

* cited by examiner

INTERVENTIONAL MEDICAL DEVICE HAVING REDUCED FRACTURE RISK

CROSS-REFERENCE TO RELATED APPLICATIONS

This application is a U.S. national phase of International Application No. PCT/US2017/049372, filed Aug. 30, 2017, which is incorporated herein by reference in its entirety.

TECHNICAL FIELD

The present invention relates to interventional medical devices, and, more particularly, to an interventional medical device that reduces fracture risk to the patient.

BACKGROUND ART

It is well known in the medical arts to use an interventional medical device, such as a guide wire, angioplasty balloon, ultrasonic catheter, needle, or vascular filter, in the diagnostics and/or treatment of a patient. The interventional medical device is configured as an invasive device to be inserted into the tissue, vessel, or cavity of a patient. The interventional medical device will be present in the patient for some period of time, with the amount of time depending upon the type of device being used.

For example, during one type of atherectomy procedure, an ultrasonic catheter is inserted into a blood vessel of a patient and is energized to break through a calcified vascular occlusion in the blood vessel. The ultrasonic catheter includes a sheath having a lumen, and a shaft, also referred to in the art as a corewire, which runs through the lumen of the support shaft. A distal end portion of the corewire protrudes from the distal end of the shaft, and the corewire is coupled to an ultrasonic energy source. When the ultrasonic energy source is energized, the distal end portion of the corewire vibrates at the ultrasonic frequency to produce a radial and axial vibrating motion of the distal end portion. However, subjecting the distal end portion of the corewire to such movement at the ultrasonic frequency may create a possibility of fracturing at the distal end portion of the corewire.

As another example, it is known to use a vascular filter that is designed to capture an embolism, e.g., a blood clot, which is traveling with the blood through the blood vessel, so as to prevent the embolism from reaching the heart or lungs. The vascular filter typically is configured as a structure that permits continued blood flow through the blood vessel, while trapping the blood clot traveling in the blood stream. However, there may be the potential for health complications if the vascular filter fractures and migrates in the blood stream.

What is needed in the art is an interventional medical device configured such that the portions of the interventional medical device that are subject to fracture and migration within the patient are tied together, so as to reduce the risk of potential health complications that the fractured portion of the device might pose to the patient.

SUMMARY OF INVENTION

The present invention provides an interventional medical device configured such that the portions of the interventional medical device that are subject to fracture and migration within a patient are tied together, so as to reduce the risk of potential health complications that the fractured portion of the device might pose to the patient.

The invention in one form is directed to an interventional medical device, such as an ultrasonic catheter that includes a flexible catheter body, a corewire, and a membrane. The flexible catheter body has a proximal end, a distal end, and a lumen that extends through the catheter body to the distal end. The corewire is positioned in the lumen of the flexible catheter body. The corewire has a distal tip, a distal end portion, and a transmission portion. The distal end portion extends proximally from the distal tip and the transmission portion extends proximally from the distal end portion. The distal end portion is configured to longitudinally extend in its entirety from the distal end of the flexible catheter body. The membrane encapsulates at least the distal end portion of the corewire. The membrane is configured to tie together a fractured portion of the distal end portion of the corewire.

The invention in another form is directed to an interventional medical device, such as an atherectomy device. The atherectomy device includes an elongate flexible catheter body having a proximal end, a distal end, and a lumen extending from the proximal end to the distal end. An ultrasound corewire extends longitudinally and unattached through the lumen of the elongate flexible catheter body to facilitate excitation of the ultrasound corewire within the elongate flexible catheter body. The ultrasound corewire has a distal end portion and an active distal portion that includes the distal end portion. The distal end portion is configured to extend distally past the distal end of the elongate flexible catheter body so that the distal end portion of the ultrasound corewire is fully exposed, and with a portion of the active distal portion being positioned in the lumen. A membrane extends along the ultrasound corewire to encapsulate the active distal portion of the ultrasound corewire.

The invention in another form is directed to an interventional medical device, such as an intravascular device. The intravascular device includes a body and a plurality of wire projections that extend from the body. The wire projections are spaced apart in an annular pattern to form a vascular filter portion. A plurality of membrane portions is configured to encapsulate each of the plurality of wire projections, with each membrane portion of the plurality of membrane portions encapsulating a respective one of the plurality of wire projections. Each membrane portion of the plurality of membrane portions has a proximal end that is attached to the body.

The invention in another form is directed to a method of manufacturing an interventional medical device. The method includes identifying at least one portion of the interventional medical device that is subject to fracture and migration within a patient; and applying a membrane over each portion of the interventional medical device that is subject to fracture and migration, such that any fractured portion of each portion of the interventional medical device that is subject to fracture and migration is tied together by the membrane.

One advantage of the present invention is that the membrane ties the fractured portion, e.g., having multiple fragments, of the interventional medical device together, and may also tie the fractured portion to a unitary portion of the interventional medical device, so as to help reduce the risk of the fractured pieces, e.g., fragments, of the fractured portion migrating within the patient, and to allow the fractured portion to be retrieved along with the interventional medical device by withdrawing the interventional medical device from the patient.

Another advantage of the present invention is that the membrane also helps reduce the risk of an occurrence of fracturing of an active portion of the interventional medical device, but if fracturing does occur, then the membrane ties the fractured portion together, so as to help reduce the risk of fragments of the fractured portion migrating within the patient

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DESCRIPTION OF EMBODIMENTS

Figure 1:
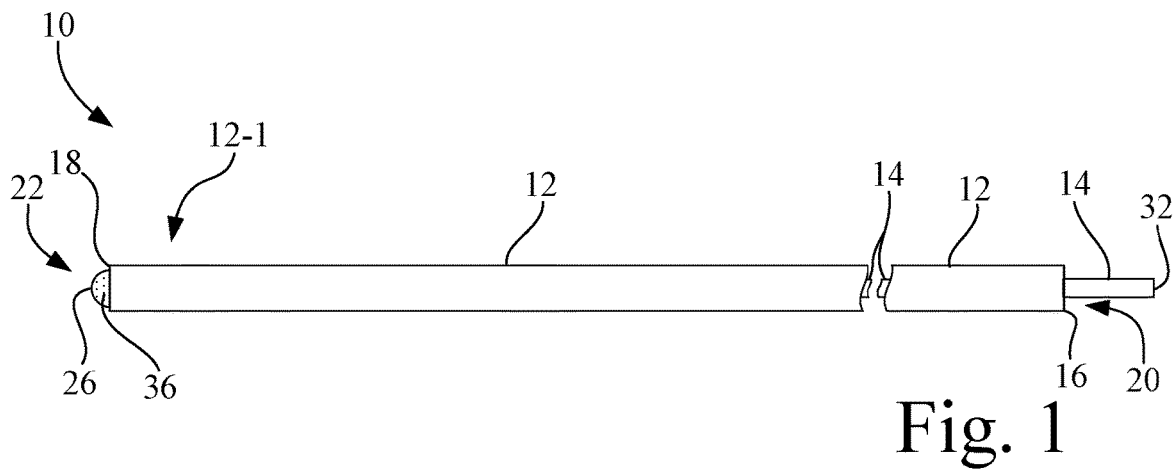
FIG. 1 is side view of an elongate ultrasonic catheter in accordance with the present invention, shown partially broken away, having a flexible catheter body and a corewire, with the corewire in the retracted position.
Figure 2:
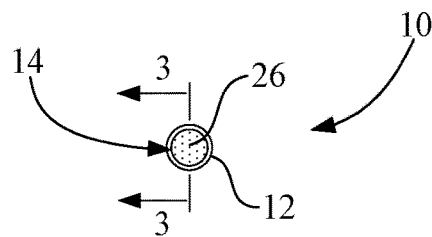
FIG. 2 is an end view of the ultrasonic catheter of FIG. 1.

The present invention is directed to an interventional medical device, and method for manufacturing the same, wherein at least one portion of the interventional medical device that is subject to fracture and migration within a patient is identified. As used herein, the term fracture refers to a breaking of the interventional medical device that results in at least one fragment. A membrane, such as a polymer, is applied over each portion of the interventional medical device that is subject to fracture and migration, such that any fractured portion, e.g., having multiple fragments, of the interventional medical device is tied together by the membrane which remains attached to the interventional medical device. The specific embodiments shown in the drawings and described below are directed to an ultrasonic catheter and a vascular filter, but those skilled in the art will recognize that the principles of the invention, as set forth below in the description of the embodiments and in the claims, may be applied to other types of interventional medical devices.

Referring to FIGS. 1-5, there is shown an embodiment of an interventional medical device in accordance with an aspect of the present invention, which is in the form of an ultrasonic catheter 10. Ultrasonic catheter 10 includes a catheter body 12 and a corewire 14, sometimes also referred to in the art as an ultrasound corewire 14.

Referring to FIG. 1, catheter body 12 is an elongate structure having a proximal end 16, a distal end 18, and a lumen 20 that extends through catheter body 12 from proximal end 16 to distal end 18. Catheter body 12 may be made, for example, from a flexible material, such as plastic or other flexible polymer material. In the present embodiment, catheter body 12 has a single lumen 20. However, those skilled in the art will recognize that lumen 20 may be one of a plurality of lumens present in catheter body 12.

Figure 3:
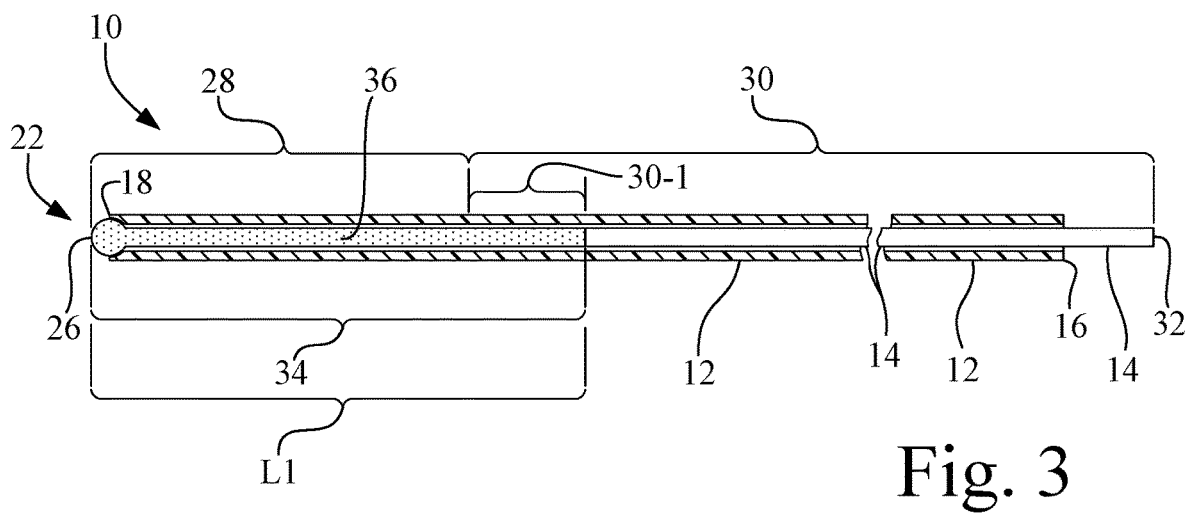
FIG. 3 is a section view of the flexible catheter body of the ultrasonic catheter of FIG. 1, taken along line 3-3 of FIG. 2, showing the flexible catheter body in cross-section to expose the corewire in the retracted position.
Figure 4:
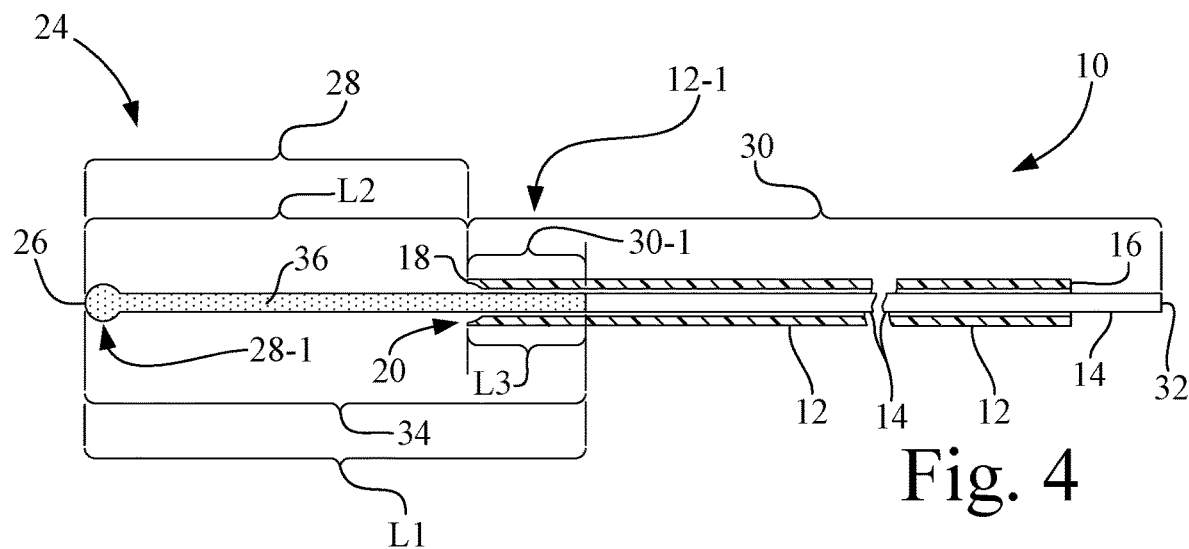
FIG. 4 is a section view corresponding to the section view of FIG. 3, showing the corewire in the fully extended position.

Referring to FIGS. 2-5, corewire 14 is positioned in lumen 20 of catheter body 12, with corewire 14 being unattached to catheter body 12 so as to facilitate an excitation of corewire 14 within catheter body 12, and to facilitate longitudinal movement of the ultrasound corewire 14 within catheter body 12 between a retracted position 22, depicted in FIGS. 1 and 3, and a fully extended position 24, depicted in FIG. 4. Alternatively, if desired, corewire 14 may be non-retractable relative to catheter body 12, and permanently fixed at the fully extended position 24.

Figure 5:
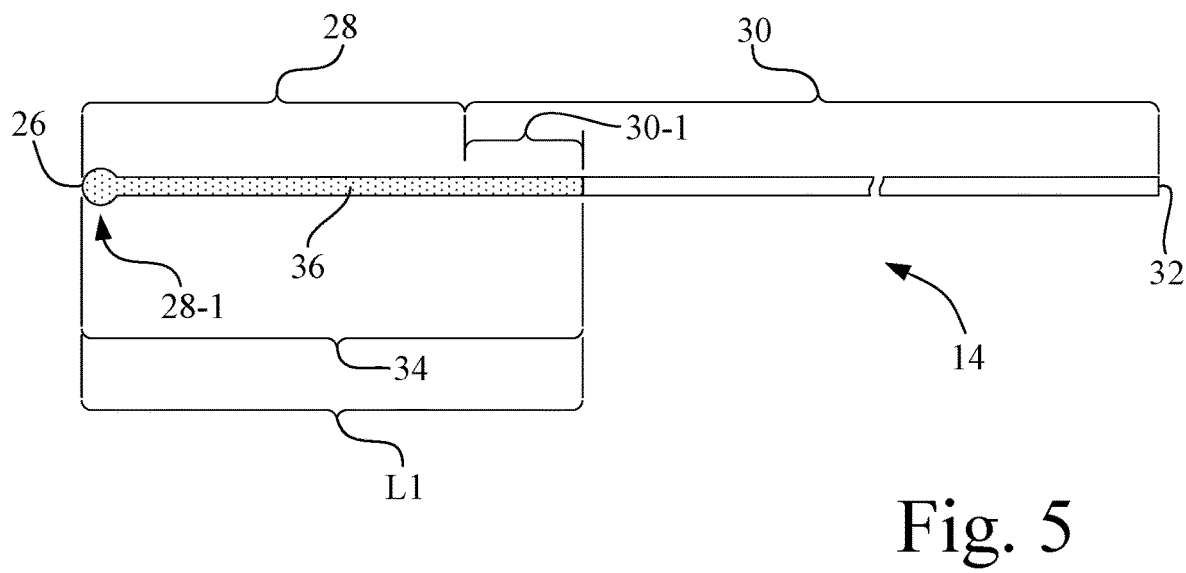
FIG. 5 is a side view of the corewire of the ultrasonic catheter of FIG. 1, removed from the flexible catheter body.

Referring to FIGS. 3-5, corewire 14 has a distal tip 26, a distal end portion 28, a transmission portion 30, and a proximal end 32. Distal end portion 28 and transmission portion 30 of corewire 14 are formed as a single unitary elongate member made of a flexible metal, such as nitinol. Distal end portion 28 may include a head portion 28-1. In some variations of corewire 14, it is contemplated that head portion 28-1 may be initially formed as a separate component that is attached, e.g., via weld or adhesive, to corewire 14 in defining distal end portion 28. Distal end portion 28 extends proximally, i.e., in a proximal direction, from distal tip 26, and transmission portion 30 further extends proximally from distal end portion 28 to terminate at proximal end 32.

Proximal end 32 of corewire 14 is configured to be coupled to an ultrasound energy source (not shown), which supplies axial and radial, e.g., transverse, ultrasonic vibration to transmission portion 30 of corewire 14, and in turn to distal end portion 28. Referring to FIG. 4, distal end portion 28 is configured to longitudinally extend in its entirety from distal end 18 of the catheter body 12 when corewire 14 is in the fully extended position 24. During operation, distal end 18 of catheter body 12 is separated by a variable gap from head portion 28-1 ultrasound corewire 14, where the gap permits free movement of active distal portion 34 of the ultrasound corewire 14 relative to catheter body 12.

Referring to FIGS. 3-5, an active distal portion 34 of corewire 14 is defined as a portion of corewire 14 that may be subjected to the most intense longitudinal and transverse ultrasonic vibration motions during ultrasonic activation. In the present embodiment, active distal portion 34 of corewire 14 includes all of distal end portion 28 and includes a distal portion 30-1 of transmission portion 30 within lumen 20 of catheter body 12. In particular, a portion of the active distal portion 34 is always positioned in lumen 20, such that when distal end portion 28 extends distally in its entirety past distal end 18 of catheter body 12 and is fully exposed, then a portion of active distal portion 34 remains positioned in lumen 20 at a distal end portion 12-1 of catheter body 12.

Referring to FIGS. 1-7, a portion of corewire 14 is encapsulated by a membrane 36, wherein membrane 36 is represented in the drawings by stippling. Referring to FIGS. 3-6, membrane 36 encapsulates at least distal end portion 28 of corewire 14, which is fully exposed when corewire 14 is in the fully extended position 24 (see FIG. 4). Membrane 36 is formed from a polymer material, and has a thin wall thickness, e.g., 10 to 150 microns.

Figure 6:
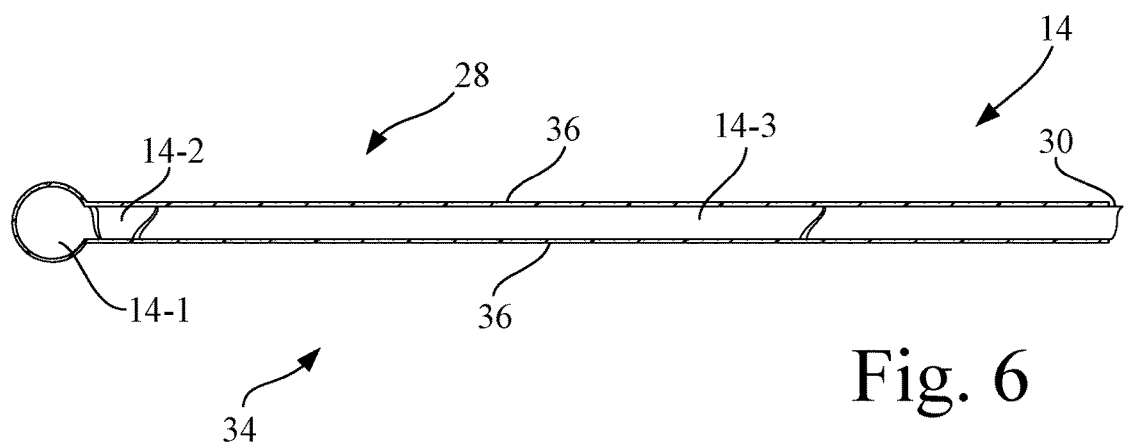
FIG. 6 is an enlargement of an active distal portion of the corewire (see FIG. 5) that was damaged during operation, with the membrane sectioned away to expose fragments of the fractured portion of the corewire.

Membrane 36 is continuous around the entire metallic circumference of corewire 14 for the longitudinal extent of membrane 36. Membrane 36 longitudinally extends, i.e., covers, less than a full length of corewire 14, and in the present embodiment, extends an entirety of the length of active distal portion 34. Referring also to FIG. 6, membrane 36 is configured to tie together any fractured portion, e.g., having multiple fragments 14-1, 14-2, 14-3, of distal end portion 28 and active distal portion 34 of corewire 14, and to bind the fractured portion that includes fragments 14-1, 14-2, 14-3 to transmission portion 30 of corewire 14.

As best shown in FIG. 4, membrane 36 extends a distance L1 proximally from distal tip 26 of corewire 14, wherein the distance L1 corresponds to a length of active distal portion 34, thus passing over distal end portion 28 and onto transmission portion 30 of corewire 14. In the present embodiment, the distance L1 (length of active distal portion 34) is in a range of about 5.0 centimeters to about 6.4 centimeters, and a length L2 of distal end portion 28 is about 3.8 centimeters to about 5.0 centimeters, with a portion of membrane 36 extending a distance L3 into lumen 20 of catheter body 12.

As used herein, the term "about" is a range of plus or minus 10 percent of the base amount.

Referring again to FIG. 6, if distal end portion 28 of corewire 14 becomes fractured during operation, membrane 36 ties the fractured pieces, e.g., fragments 14-1, 14-2, 14-3, together and to transmission portion 30 of corewire 14 to help reduce the risk of fragments 14-1, 14-2, 14-3 of the fractured portion migrating within the patient, and to allow the fractured portion to be retrieved with corewire 14 by withdrawing corewire 14 from the patient.

In addition, in the present embodiment, referring again to FIG. 4, membrane 36 always extends at least distance L3 into lumen 20 of catheter body 12. In the present embodiment, distance L3 is a distance of about 1.0 to about 1.3 centimeters into lumen 20 of catheter body 12 from distal end 18. Since membrane 36 is a polymer material that covers the entire circumferential metallic surface of corewire 14 at active distal portion 34, membrane 36 also serves as a mechanical damper in lumen 20 at distal end portion 12-1 of catheter body 12, which in turn reduces the risk of an occurrence of a fracture of distal end portion 28 of corewire 14. Further, this damping action facilitates a reduction in operating frequency of the ultrasound source to achieve the same level of transverse ultrasound vibration motion of distal end portion 28 of corewire 14.

Also, if the polymer of membrane 36 has anti-friction properties, membrane 36 may further reduce frictional wear at distal end portion 12-1 of catheter body 12, and in turn reduce the amount of heat that is generated during ultrasonic activation of corewire 14.

In the present embodiment, membrane 36 may be formed as a coating that is applied over distal end portion 28 of corewire 14, such as by one of chemical vapor or physical vapor deposition, with the deposit being a polymer, such as a parylene polymer, or alternatively, a fluoropolymer.

As a variation to applying a coating, membrane 36 may be formed as a polymer sleeve having a closed distal end that is positioned over distal end portion 28 of corewire 14 and collapsed to tightly bind to the outer surface of corewire 14, e.g., at active distal portion 34. For example, the sleeve may be made from an elastomer, such as rubber. It is further contemplated that the sleeve may be formed from thermoplastic shrink tubing, such as for example, shrink tubing made from polyolefin or PTFE.

Figure 7:
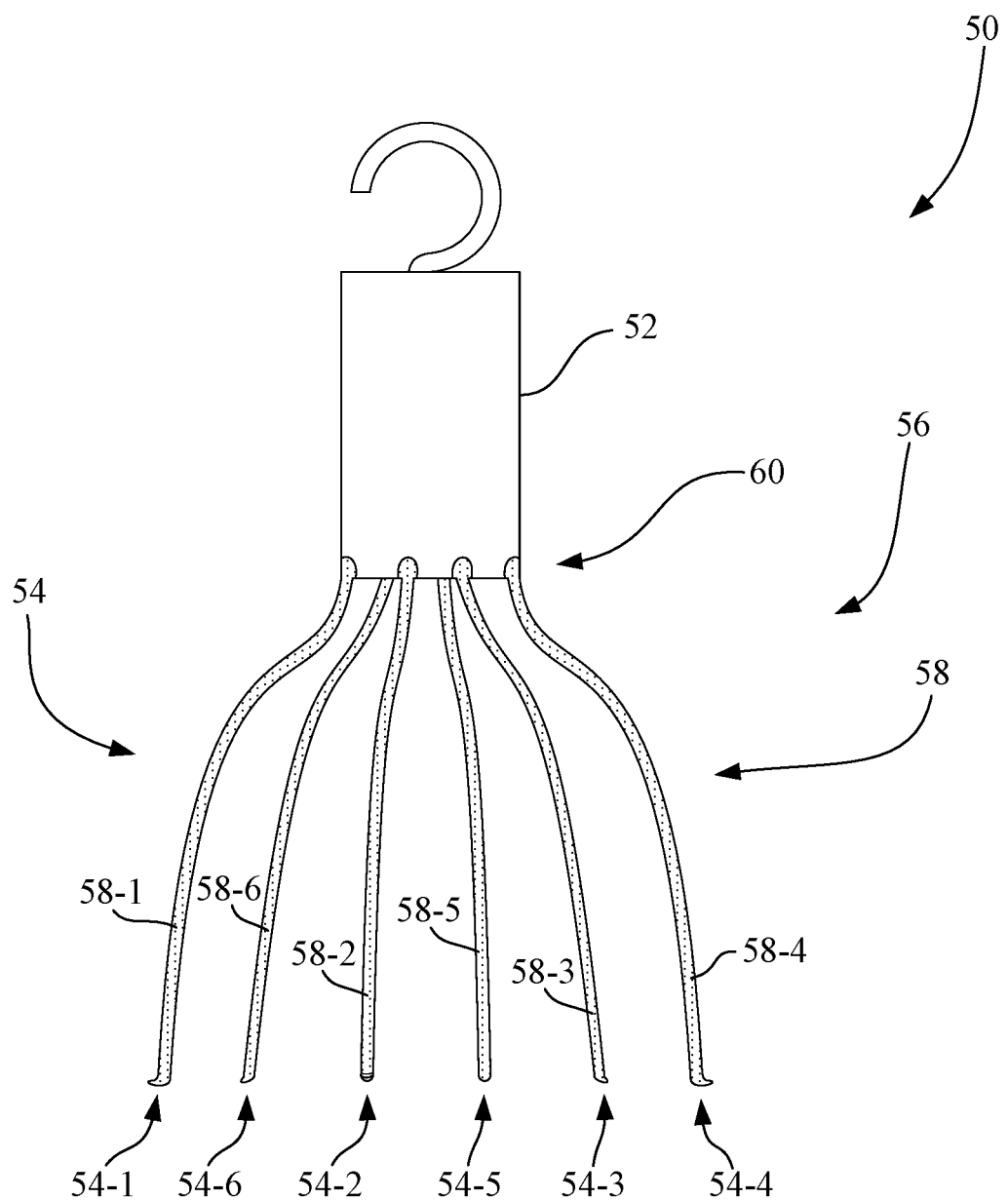
FIG. 7 is a side view of a vascular filter in accordance with the present invention.

Referring now to FIG. 7, there is shown another embodiment of an interventional medical device in accordance with an aspect of the present invention, which is in the form of an intravascular filter 50. Intravascular filter 50 includes a body 52, and a plurality of wire projections 54 that extend from body 52. In the present embodiment, the plurality of wire projections 54 includes six wire projections individually identified as wire projection 54-1, wire projection 54-2, wire projection 54-3, wire projection 54-4, wire projection 54-5, and wire projection 54-6. Wire projection 54-1, wire projection 54-2, wire projection 54-3, wire projection 54-4, wire projection 54-5, and wire projection 54-6 of the plurality of wire projections 54 are spaced apart in an annular pattern to form a vascular filter portion 56.

A plurality of membrane portions 58 is configured to encapsulate each of the plurality of wire projections 54. In FIG. 7, each of the plurality of membrane portions 58 is represented by stippling. Each of the plurality of membrane portions 58 is individually identified as membrane portion 58-1, membrane portion 58-2, membrane portion 58-3, membrane portion 58-4, membrane portion 58-5, and membrane portion 58-6, respectively. Each membrane portion 58-1, 58-2, 58-3, 58-4, 58-5, 58-6 of the plurality of membrane portions 58 encapsulates a respective wire projection 54-1, 54-2, 54-3, 54-4, 54-5, 54-6 of the plurality of wire projections 54.

Each membrane portion 58-1, 58-2, 58-3, 58-4, 58-5, 58-6 of the plurality of membrane portions 58 is formed from a polymer material, and has a thin wall thickness, e.g., 10 to 150 microns, that is continuous around the respective wire projection 54-1, 54-2, 54-3, 54-4, 54-5, 54-6 of the plurality of wire projections 54. Each membrane portion 58-1, 58-2, 58-3, 58-4, 58-5, 58-6 of the plurality of membrane portions 58 has a proximal end 60 that is attached, e.g., adhered, to body 52.

For example, each membrane portion 58-1, 58-2, 58-3, 58-4, 58-5, 58-6 of the plurality of membrane portions 58 may be applied as a coating to encapsulate the respective wire projection 54-1, 54-2, 54-3, 54-4, 54-5, 54-6 of the plurality of wire projections 54. In particular, each membrane portion 58-1, 58-2, 58-3, 58-4, 58-5, 58-6 of the plurality of membrane portions 58 may be applied by chemical vapor deposition or physical vapor deposition, with the deposit being a polymer, such as for example, a parylene polymer, or alternatively, a fluoropolymer.

Alternatively, each membrane portion 58-1, 58-2, 58-3, 58-4, 58-5, 58-6 of the plurality of membrane portions 58 may be a respective sleeve that covers, e.g., encapsulates, the exposed portion of the respective wire projection 54-1, 54-2, 54-3, 54-4, 54-5, 54-6 of the plurality of wire projections 54, and attached, i.e., adhered, to body 52. For example, each sleeve may be made from a polymer, such as an elastomer, e.g., rubber. It is further contemplated that each sleeve may be formed from thermoplastic shrink tubing, such as for example, shrink tubing made from polyolefin or PTFE.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An ultrasonic catheter, comprising:
a flexible catheter body having a proximal end, a distal end, and a lumen that extends through the catheter body from the proximal end to the distal end;
a corewire positioned in the lumen of the flexible catheter body, the corewire having a distal tip, a distal end portion, and a transmission portion, the distal end portion comprising an enlarged head portion at the distal tip, the distal end portion extending proximally from the distal tip and the transmission portion extending proximally from the distal end portion, the distal end portion configured to longitudinally extend in its entirety from the distal end of the flexible catheter body; and
a membrane that is continuous and applied as a coating over the corewire to encapsulate at least the distal end portion including the enlarged head portion of the corewire by extending proximally from the distal tip of the corewire by a first distance, the first distance passing over the distal end portion and onto the transmission portion of the corewire, the first distance being less than a full length of the corewire,
the membrane configured to tie together a fractured portion of the distal end portion of the corewire and to tie the fractured portion to the transmission portion of the corewire when a fracture occurs.

2. The ultrasonic catheter of claim 1, wherein the first distance is 5.0 centimeters to 6.4 centimeters.

3. The ultrasonic catheter of claim 1, wherein the membrane is applied to the distal end portion of the corewire by one of chemical vapor deposition or physical vapor deposition.

4. The ultrasonic catheter of claim 1, wherein the membrane is made of a polymer material.

5. The ultrasonic catheter of claim 1, wherein the corewire and the membrane are extendable and retractable relative to the flexible catheter body.

6. An atherectomy device, comprising:
an elongate flexible catheter body having a proximal end, a distal end, and a lumen extending from the proximal end to the distal end;
an ultrasound corewire that extends longitudinally and unattached through the lumen of the elongate flexible catheter body to facilitate excitation of the ultrasound corewire within the elongate flexible catheter body, the ultrasound corewire having a distal end portion comprising an enlarged head portion at a distal tip and an active distal portion that includes the distal end portion, the distal end portion configured to extend distally past the distal end of the elongate flexible catheter body so that the distal end portion of the ultrasound corewire is fully exposed, and with a portion of the active distal portion being positioned in the lumen; and
a membrane extending along the ultrasound corewire, the membrane is continuous and applied as a coating over the ultrasound corewire to encapsulate the active distal portion including the enlarged head portion of the ultrasound corewire by extending proximally from the distal tip of the ultrasound corewire by a first distance, the first distance being less than a full length of the ultrasound corewire, wherein the membrane is configured to tie together a fractured portion of the distal end portion of the ultrasound corewire and to tie together the fractured portion to a unitary portion of the ultrasound corewire.

7. The atherectomy device of claim 6, wherein the elongate flexible body distal end is separated by a gap from the ultrasound corewire, where the gap permits free movement of the active distal portion of the ultrasound corewire relative to the elongate flexible catheter body.

8. The atherectomy device of claim 6, wherein the first distance is 5.0 centimeters to 6.4 centimeters.

9. The atherectomy device of claim 6, wherein the membrane is applied to the active distal portion of the ultrasound corewire by one of chemical vapor deposition or physical vapor deposition.

10. The atherectomy device of claim 6, wherein the membrane is made of a parylene polymer material.

11. A method of manufacturing an ultrasonic catheter, comprising:
a flexible catheter body having a proximal end, a distal end, and a lumen that extends through the flexible catheter body from the proximal end to the distal end; and
a corewire positioned in the lumen of the flexible catheter body, the corewire configured to move in the lumen between a retracted position and a fully extended position, the corewire having a distal tip, a distal end portion, and a transmission portion, the distal end portion comprising an enlarged head portion at the distal tip, the distal end portion extending proximally from the distal tip and the transmission portion extending proximally from the distal end portion, the distal end portion configured to longitudinally extend in its entirety from the distal end of the flexible catheter body when the corewire is in the fully extended position,
the method comprising
identifying at least one portion of the corewire that is subject to fracture and migration within a patient; and
coating a membrane over each portion of the corewire that is subject to fracture and migration to encapsulate each portion of the corewire, such that, when a fracture occurs, any fractured portion of each portion of the corewire that is subject to fracture and migration is tied together by the membrane, wherein the membrane is continuous and extends proximally from the distal tip of the corewire by a first distance, the first distance passing over the distal end portion including the enlarged head portion and onto the transmission portion of the corewire, the first distance being less than a full length of the corewire.

12. The method of claim 11, wherein the membrane extends proximally from the distal tip of the corewire by a first distance, the first distance passing over the distal end portion and onto the transmission portion of the corewire, the first distance being 5.0 centimeters to 6.4 centimeters.

13. The method of claim 11, wherein the membrane is applied to the distal end portion of the corewire by one of chemical vapor deposition or physical vapor deposition.

14. The method of claim 11, wherein the membrane is made of a fluoropolymer material.

* * * * *